United States Patent [19]

Zaugg et al.

[11] Patent Number: 4,819,684
[45] Date of Patent: Apr. 11, 1989

[54] INJECTION SHUT-OFF VALVE

[75] Inventors: Paul Zaugg, Lutzelfluh; Werner Kiesinger, Winterthur, both of Switzerland

[73] Assignee: Intermedicat GmbH, Emmenbrucke, Switzerland

[21] Appl. No.: 29,749

[22] Filed: Mar. 24, 1987

[30] Foreign Application Priority Data

Apr. 11, 1986 [EP] European Pat. Off. ........ 86105010.2

[51] Int. Cl.$^4$ .............................................. A61M 37/00
[52] U.S. Cl. .................................. 137/112; 137/625.4; 137/853; 251/149.1; 604/83; 604/247
[58] Field of Search ................. 137/112, 512.4, 625.4, 137/853; 251/149.1; 604/83, 33, 34, 247, 249

[56] References Cited

U.S. PATENT DOCUMENTS

| | | | |
|---|---|---|---|
| 2,867,213 | 1/1959 | Thomas | 604/247 |
| 3,416,567 | 12/1968 | Von Dardel | 604/83 X |
| 3,707,972 | 1/1973 | Villari | 604/249 |
| 3,965,910 | 6/1976 | Fischer | 604/249 |
| 3,996,923 | 12/1976 | Guerra . | |
| 4,063,555 | 12/1977 | Ulinder | 137/853 X |
| 4,301,811 | 11/1981 | Layton . | |
| 4,506,691 | 3/1985 | Tseo . | |
| 4,540,027 | 9/1985 | Forberg | 604/247 X |
| 4,582,081 | 4/1986 | Fillman | 137/853 |
| 4,666,429 | 5/1987 | Stone | 604/83 |
| 4,690,165 | 9/1987 | Leytes | 137/112 |

FOREIGN PATENT DOCUMENTS

| | | |
|---|---|---|
| 15443 | 2/1980 | European Pat. Off. . |
| 1216489 | 12/1966 | Fed. Rep. of Germany . |
| 2601993 | 7/1976 | Fed. Rep. of Germany . |
| 7812248 | 8/1978 | Fed. Rep. of Germany . |
| 3142524 | 11/1983 | Fed. Rep. of Germany . |

Primary Examiner—Robert G. Nilson
Attorney, Agent, or Firm—Ladas & Parry

[57] ABSTRACT

An injection shut-off valve for insertion into an infusion line comprises a housing with connections for inlet and outlet lines. The housing includes an orifice for introducing an injection syringe. A valve is installed in the housing and includes a deformable diaphragm. In a non-injection state, the valve device seals off fluid flow between the inlet and outlet lines on the one hand and the orifice on the other. During injection, the diaphragm is deformed to create an opening such that fluid flow from the inlet to the housing is shut off. During deformation of the diaphragm the orifice is brought into fluid carrying communication with the outlet line from the housing, thus making it possible for the injection fluid to pass through the housing into the outlet line, and to a patient.

7 Claims, 4 Drawing Sheets

INJECTION SHUT-OFF VALVE

The invention described here relates to an injection shut-off valve for insertion into an infusion line or the like. The valve has a housing with connections for the inlet and-outlet of the said line and an orifice for introducing an injection syringe.

Injection valves for administering injections in infusion lines or the like are known:

In the injection valve according to German Patent No. 1,216,489, the valve body has an elastic sleeve. The valve body is inserted into the main flow channel, and the periphery of the sleeve rests sealingly against the outlet orifice for injection fluid. When the injection solution is forced in, the sleeve is pushed away from the outlet orifice in the valve body as a result of the injection pressure thereby generated and the valve is opened. The flow through the infusion line is not actually affected by the injection.

In the embodiment mentioned, a hydrostatic pressure is first built up between the conical extension of the injection syringe and the valve, and the valve forces and the system pressure acting against the valve have to be overcome by means of this hydrostatic pressure.

In specific cases, for example when the injection valve is used in vein catheters fixed to the patient's skin, the specific force arising during the supply of injection fluid and resulting from frictional forces in the injection syringe and from the hydrodynamic pressure for keeping the valve open is transmitted to the patient's skin in the form of surface pressure. Since small quantities from a filling of the injection syringe are administered to a patient even several times at intervals, the patent may be subjected to considerable multiple stresses depending on the magnitude of the valve forces.

When the supply of injection fluid has ended, the hydrostatic pressure initially persists and counter-balances the valve forces, that is to say a residual quantity of injection fluid remains between the conical extension of the injection syringe and the valve. If the administration of injection fluid ceases for a longer period, the injection syringe being removed, there is the danger that the remaining injection fluid will be contaminated and fed into the system and consequently to the patient together with the next injection.

A further known injection valve according to German Utility Model No. 78.12,248 contains an elastomeric slotted valve body which is inserted free of tension into a housing. The conical extension of the injection syringe presses apart the tabs of the valve body which are formed as a result of the slotting, so that injection fluid can be introduced into the main flow channel. It is also possible to extract fluid from the system via the valve, for example for analyses.

Once again, injection by means of this valve does not affect the simultaneous throughflow of the infusion solution.

After the conical extension has been pulled out of the valve body, the orifice closes automatically, and virtually no residual quantity of injection fluid remains between the conical extension and the valve. Increased stress on the surface of the patient's skin in the form of surface pressure only occurs once when the injection syringe is introduced into the insertion orifice, whilst during further administration of injection fluid the stress is reduced by the considerable amount of the valve forces. In this known injection valve, however, a disadvantage for the person handling the injection syringe is that substantial force is required to open the valve body by means of the conical extension of the injection syringe, that is to say, it is very difficult to introduce the conical extension of the injection syringe into the insertion orifice of the injection valve until the conical extension has opened the valve body mechanically. This is because the known valve body, which is inserted free of tension into the housing, has to have a considerable wall thickness, so that the intrinsic elasticity of the material is sufficient to close the slot and keep it closed after the conical extension has been pulled out.

The object on which the invention of the injection valve according to European Patent Application Publication No. 0,015,443 is based is to design the elastomeric valve body of the valve so that, whilst having a relatively small wall thickness and being correspondingly easier to open by means of the conical extension of the injection syringe, has sufficient closing force as a result of its intrinsic elasticity.

In the European Patent Application mentioned, this object is achieved because the valve body is in the form of an elastic plate which is under inherent tension and has a sealing body suspended on elastic bands, and the edge region of which presses a clamping body against an annular shoulder at the housing outlet orifice. The plate held clamped in its edge region can, in terms of its elastic bands, be made so thin relative to the sealing body that it can be pressed on easily and virtually without the exertion of force by means of the conical extension of the injection syringe introduced into the insertion orifice. The sealing body, because of its elastic suspension or construction, moves aside, even when the conical extension is pressed only slightly, and allows fluid to be injected. As a result of the inherent tension of the plate, despite the fact that it is thin, when the conical extension of the injection syringe is pulled out the orifice closes automatically and shuts off the main flow channel so as to be fluid-tight. The intrinsic elasticity of the clamped plate makes it possible to inject infusion solution or the like as often as desired, whilst at the same time ensuring a sealing effect of the valve body which is always constant. This is important especially with regard to vein catheters with an injection facility. When the injection syringe is pulled back and removed, virtually no residual quantity of injection fluid remains between the conical extension of the injection syringe and the valve, thus avoiding the danger that contaminated injection fluid will be fed to the patient. The injection valve makes it possible not only to supply fluid, but also to extract fluid from the system, for example for the purpose of analyses. The combination of the plate and clamping body allows the plate to be removed to exchange it for an identical new plate or for a plate with a modified sealing body in order to obtain a changed flow orifice.

Even in this case, the injection operation does not fundamentally impair the throughflow of the infusion solution.

German Patent No. 1,216,489 teaches and claims an injection valve with a special catheter arrangement. By means of this catheter arrangement, an injection fluid is to be introduced into a catheter connected to a container for an infusion solution, for example a vein catheter. The arrangement is to be inserted into the line between the vein catheter and the connection to the container with the infusion fluid. The arrangement has a housing with a continuous line for fluid flowing through and a side orifice which is arranged along the catheter fluid line and via which an injection fluid enters. The inlet orifice has a conical nipple for connection to the outlet cone of an injection syringe. A body of a stop valve is made of flexible material and is located in the flow path of the catheter, the valve being laid sealingly over the side inlet orifice. When the injection fluid exerts a sufficiently high pressure, the valve is pushed away from the side orifice out of its sealing position transversely over the orifice. In a preferred embodiment, the valve is a movable collar-like extension of a tube which forms the connecting part to the container for the infusion solution.

Finally, the catheter arrangement according to German Offenlegungsschrift No. 2,601,993, of which the subject of the invention is to be treated as an improvement to the injection valve according to the abovementioned German Patent No. 1,216,486, provides a catheter for feeding a fluid from two separate feedlines, for example from a container for an infusion solution and from an injection syringe, and is so designed that difficulties are avoided. The catheter has in combination a housing, a line for a fluid through the housing with two inlet orifices, and an outlet for a fluid. One of the inlet orifices is shaped so that it can receive a dispensing device for feeding a fluid to the inlet and consequently to the passage orifice of the catheter. This inlet has a stop valve which lets the flow through only in an inward direction.

In a preferred embodiment, one inlet is cup-shaped, the side and end walls consisting of relatively hard material, for example plastic or metal. The inlet orifice is in line with the end of the cup, so that the cup end absorbs any bumping or knocking of the dispensing device (for example, a syringe needle), when the latter is inserted into the inlet. The fluid-carrying connection between the inlet and the flow line for the fluid is located in the sides of the cup in the form of one or more orifices through the side walls. The stop valve or stop valves close off the orifice or orifices sealingly. The stop valve consists of elastic material, for example elastic plastic or rubber, and the material surrounds the outside of the cup inlet, resting closely against it and sealing it. The side orifices in the cup are closed off as a result. When sufficient fluid pressure from the cup inlet is exerted, the elastic material can move away from the orifices and thus open them. This occurs, for example, when a fluid is injected there from an injection device.

A common feature of the two injection valves just discussed is that, again, no attention is actually given to reflux prevention (see also FIG. 2 in German Patent No. 1,216,489).

Thus, as has been shown, the state of the art relates mainly to injection valves for administering injections in infusion lines or the like. No attention or only totally insufficient attention has hitherto been devoted to ensuring that, in an injection of this type, at least one very important condition should be satisfied, namely minimising the variations in the injection solution as a result of remixing with the infusion solution.

It has now been shown that, as a result of the improvement according to the invention, the additional function mentioned can be guaranteed without impairing the other important functions of such devices and with convincing reliability as regards safety, operation and sterilisation. The additional function is:

the reflux prevention effect against the infusion solution entering the housing, consequently preventing the mixing of the injection solution and infusion solution, and the opening of the fluid-carrying connection from the injection catheter into the outlet line to the patient, that is to say finally the guaranteed administration of the injection.

The injection shut-off valve according to the invention for insertion into an infusion line or the like has, for this purpose, a housing with connections for the inlet and outlet of the said line and an orifice for introducing an injection syringe; it is characterized by a valve device which is installed in the said housing and has a deformable diaphragm, in the non-injection state the said valve device sealing off the flow of fluid through the said line in the housing relative to the syringe insertion orifice both physically and septically, and in the said valve device, as a result of the pressure generated in the housing during injection, the diaphragm being deformed and, if appropriate, opened in such a way that the inflow from the said line into the housing is shut off in a fluid-tight manner, as a result of which the valve acts as a non-return flap in the inflow direction, and that the flow-off from the housing into the said line is brought into fluid-carrying communication with the syringe orifice, thus making it possible for the injection fluid to pass through the housing and the said line to the patient.

Figure 1A:
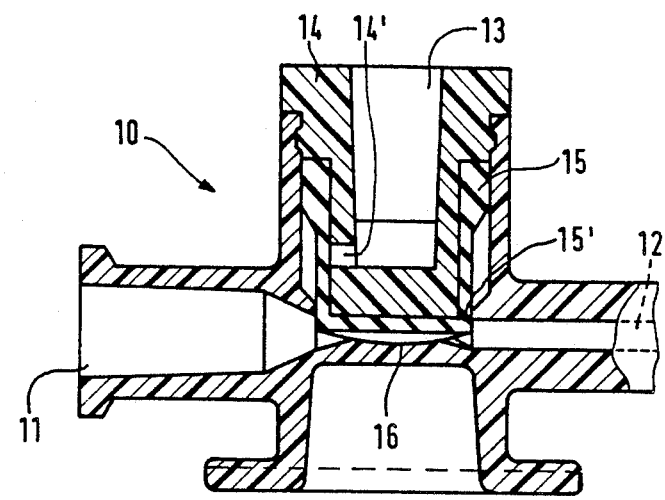
FIG. 1A is a cross-section of a first embodiment of a shut-off valve of the invention.
Figure 1B:
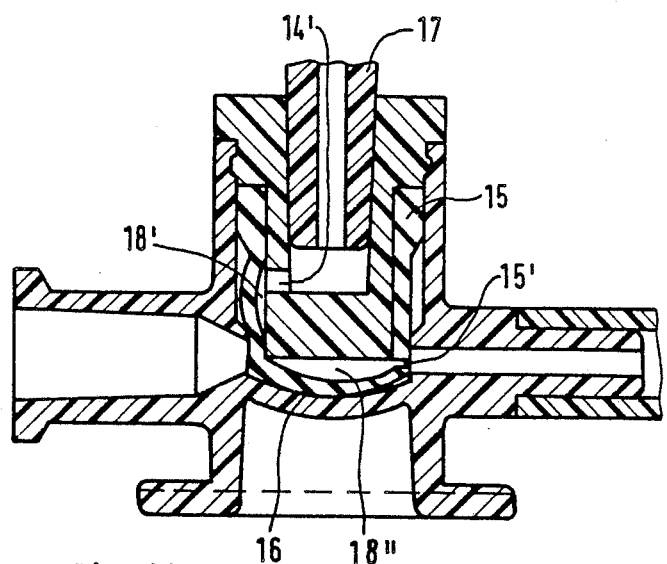
FIG. 1B is a cross-section of the shut-off valve shown in FIG. 1A, with a catheter tip inserted therein.

According to FIGS. 1A and 1B, the injection shut-off valve has a housing 10, inlet and outlet lines 11, 12 and an injection orifice 13. In it, the said orifice is arranged essentially perpendicularly to the plane of the two lines mentioned, and the valve device is formed by the part of the housing designed as the wall of the injection orifice, by the orifice body 14 inserted in it, together with the lateral through-bore 14' made in the latter at the bottom, and by the cap diaphragm 15 inserted and fastened between the two parts mentioned and having a notch 15'. In this injection shut-off valve, after the tip 17 of the injection catheter has been introduced into the injection orifice 13 and under the effect of the primary hydrodynamic injection pressure, the diaphragm 15 is now pressed away from the through-bore and a fluid-carrying communication between the injection catheter and the outlet line to the patient is thus made via the orifices 18' and 18" and as a result of the opening of the notch 15', and at the same time, as a result of the pressure of the diaphragm 15 against the seat surface 16 in the housing, the inlet line to the housing is blocked and it becomes impossible for injection fluid to flow into the said inlet line. The path between the spaces 18' and 18" may be one or more very small slip or slips between the lower edge of the orifice body 14 and that region of the adjacent cap diaphragm 15 which is opposite to the notch 15 prime.

Figure 2A:
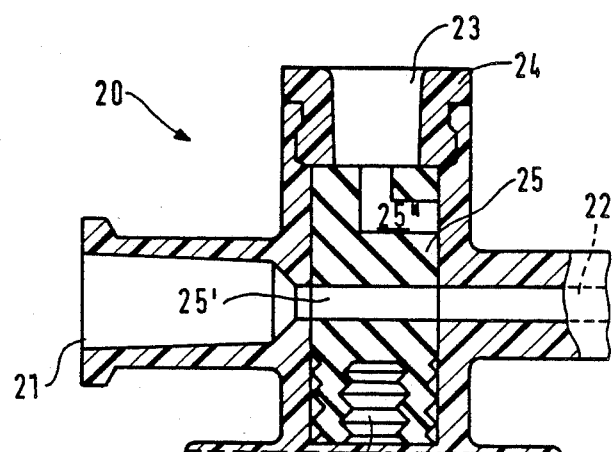
FIG. 2A is a cross-section of a second embodiment of a shut-off valve of the invention.
Figure 2B:
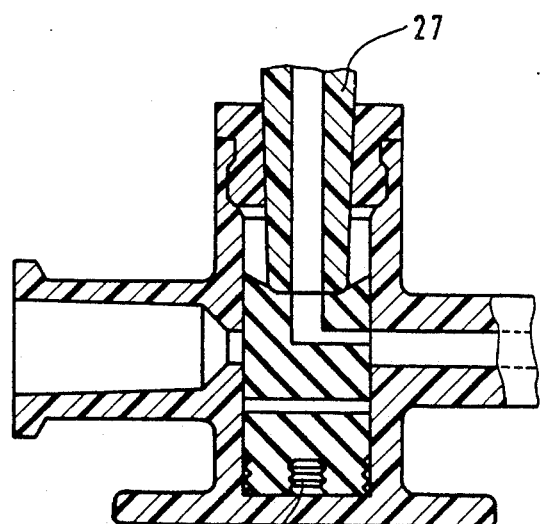
FIG. 2B is a cross-section of the shut-off valve shown in FIG. 2A, with a catheter tip inserted therein.
Figure 3A:
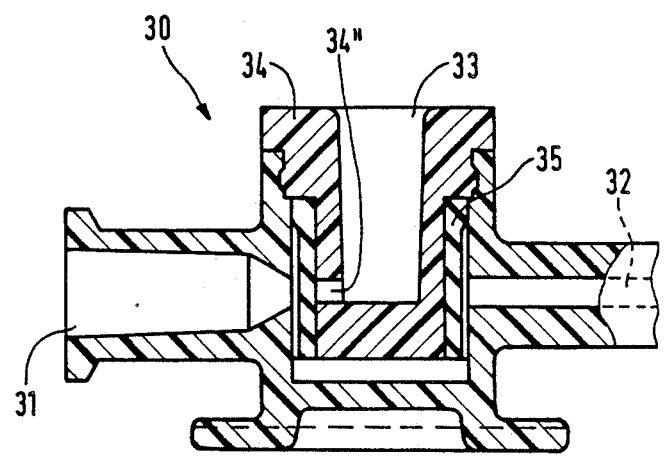
FIG. 3A is a cross-section of a third embodiment of a shut-off valve of the invention.
Figure 3B:
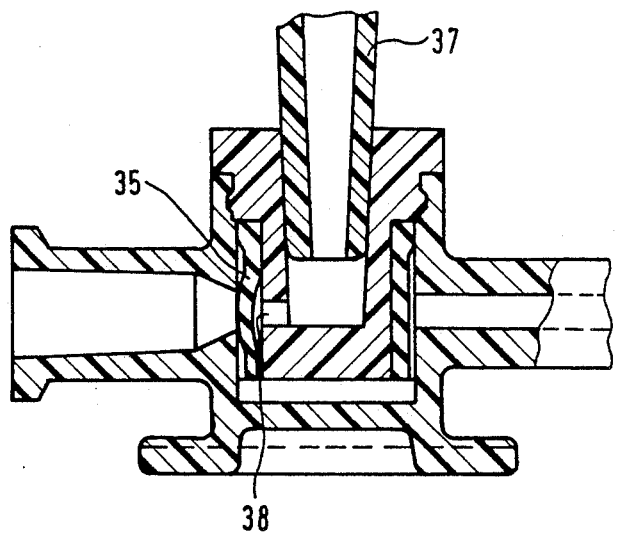
FIG. 3B is a cross-section of the shut-off valve shown in FIG. 3A, with a catheter tip inserted therein.
Figure 4A:
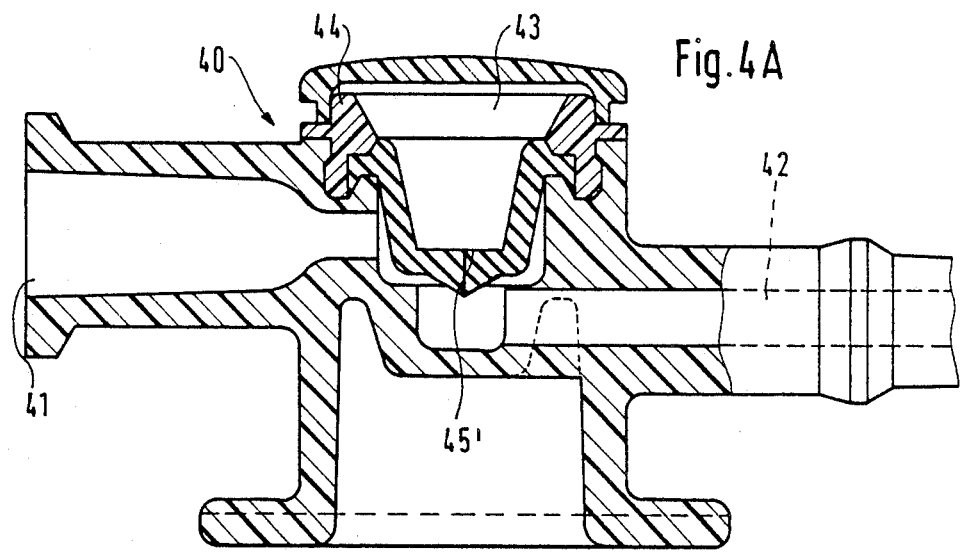
FIG. 4A is a cross-section of a fourth embodiment of a shut-off valve of the invention.
Figure 4B:
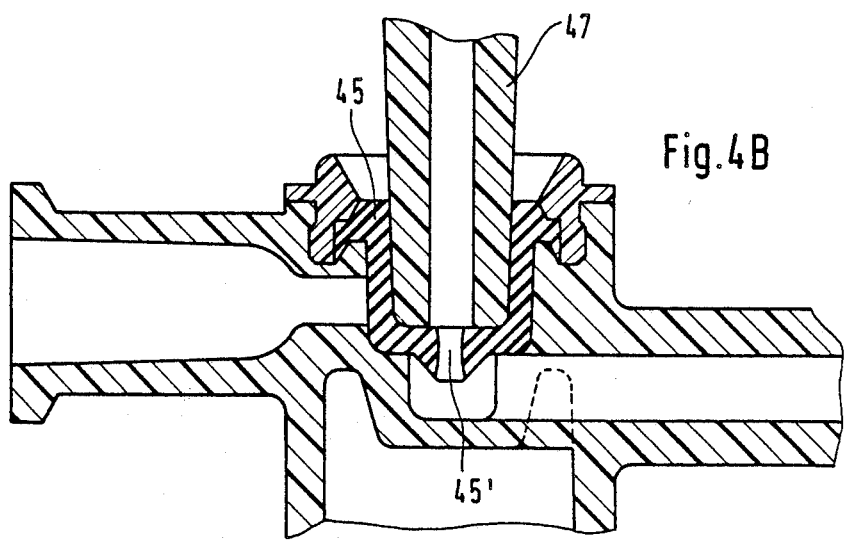
FIG. 4B is a cross-section of the shut-off valve shown in FIG. 4A, with a catheter tip inserted therein.

In the injection shut-off valve according to FIGS. 2A and 2B, a housing 20, inlet and outlet lines 21, 22 and an injection orifice 23 are provided. In it, the said orifice is essentially perpendicular to the plane of the two lines mentioned, and the valve device is formed by the part of the housing designed as the wall of the injection orifice, by the orifice body 24 inserted in it and open at the bottom, and by the bellows diaphragm 25 inserted in the housing underneath the orifice body and having in it a continuous orifice 25' for connecting the inlet and outlet lines and an angled orifice 25". In this injection shut-off valve, after the tip 27 of the injection catheter has been introduced into the injection orifice 23 and under the effect of the primary mechanical pressure of the syringe, the bellows diaphragm 25 is compressed together with corresponding reduction of the bellows volume 28, as a result of which the continuous orifice 25' is closed and the orifice 25", shifted downwards, opens the fluid-carrying connection from the injection catheter to the said outlet line only.

In the third preferred embodiment of the injection shut-off valve according to the invention, a housing 30, inlet and outlet lines 31, 32 and an injection orifice 33 are provided. This orifice is essentially perpendicular to the plane of the two lines mentioned, and the valve device is formed by the part of the housing designed as the wall of the injection orifice, by the orifice body 34 inserted in it and having the through-bore 34' made in the latter at the bottom and laterally, and by the circular-cylindrical diaphragm 35 pulled on over the orifice body. During injection, after the tip 37 of the injection catheter has been introduced into the injection orifice 33 and under the effect of the primary hydrodynamic injection pressure, the cylindrical diaphragm 35 is pressed away from the orifice body in the region of the through-bore 34', with the result that the inlet line is closed and,. by means of the passage 38 opened as a result of the pressure, fluid-carrying communication is made between the catheter tip and the outlet line only.

Finally, the injection shut-off valve according to the invention can also have a housing 40, inlet and outlet lines 41, 42 and an injection orifice 43. Here again, the said orifice is essentially perpendicular to the plane of the two lines mentioned, and the valve device is formed by the part of the housing designed as the wall of the injection orifice, by the orifice body 44 inserted in it and open at the bottom, and by the dish diaphragm 45 inserted in the housing underneath the orifice body and having a slit orifice 45'. After the tip 47' of the injection catheter has been introduced into the injection orifice 43 and under the effect of both the mechanical pressure from the catheter tip and the hydrodynamic pressure of the injection fluid, the dish diaphragm 45 is pressed downwards and the slit orifice 45' in it is opened, with the result that the inlet line is closed and fluid-carrying communication is made between the catheter tip and the outlet line only.

The above-described embodiments of the injection shut-off valve according to the invention are conventionally characterized in that the housing and orifice body consist of transparent or translucent plastic and the diaphragm consists essentially of natural rubber. They can be essentially sterilised by the usual methods.

The injection shut-off valves described here can be designed in the form of a unit insertable in infusion lines or in valves in these, and if appropriate they are in the form of units which can be fastened to a base.

The injection orifice of the new injection shut-off valves can preferably also be covered and is very easy to clean.

The injection shut-off valves according to the invention are used primarily for insertion into infusion lines.

We claim:

1. An injection shut off valve comprising:
   a housing having a fluid inlet line, a fluid outlet line and an elongate orifice body having a bore adapted to receive an end of an injection syringe, the bore being substantially perpendicular to the inlet and outlet lines, and
   a valve device located in the housing, the valve device comprising a cap-shape deformable diaphragm which includes at least one notch, the valve device being comprised of a portion of the housing, the orifice body located in the housing, and the diaphragm which is located between the orifice body and the inlet and outlet lines, the diaphragm being movable between a first non-injection state wherein the inlet and outlet lines are in fluid communication with each other and the bore is sealed from both the inlet and outlet lines, and a second injection state whereby the diaphragm is deformed, deformation of the diaphragm sealing and preventing fluid flow between the fluid inlet line on the one hand and the fluid outlet line and the bore on the other hand, deformation of the diaphragm permitting fluid flow communication between the bore and the fluid outlet line.

2. A valve as claimed in claim 1 wherein insertion of the end of the syringe into the bore, together with a primary hydrodynamic injection pressure of fluid from the syringe, moves the diaphragm into the second injection state, the notches permitting fluid flow between the bore of the orifice body and the fluid outlet line.

3. A shut-off valve as claimed in claim 1 wherein the housing and orifice body are comprised of transparent plastic, and the diaphragm is comprised essentially of natural rubber.

4. A shut-off valve as claimed in claim 1 wherein the housing and orifice body are comprised of translucent plastic, and the diaphragm consists essentially of natural rubber.

5. A shut-off valve as claimed in claim 1, the shut-off valve being fastened to a base, the base and shut-off valve comprising a unit insertable in infusion lines.

6. A shut-off valve as claimed in claim 1 further comprising a removable cover for the injection orifice.

7. Use of an injection shut-off valve according to claim 1 for insertion into infusion lines.

* * * * *